United States Patent
Pillai

(10) Patent No.: US 10,828,038 B2
(45) Date of Patent: Nov. 10, 2020

(54) CAROTID ARTERY EMBOLIC PROTECTION METHOD USING PERCUTANEOUS TRANSJUGULAR CAROTID FLOW REVERSAL

(71) Applicant: Lakshmikumar Pillai, Morgantown, WV (US)

(72) Inventor: Lakshmikumar Pillai, Morgantown, WV (US)

(73) Assignee: Lakshmikumar Pillai, MD, Morgantown, WV (US)

( * ) Notice: Subject to any disclaimer, the term of this patent is extended or adjusted under 35 U.S.C. 154(b) by 160 days.

(21) Appl. No.: 16/153,585

(22) Filed: Oct. 5, 2018

(65) Prior Publication Data

US 2020/0107838 A1   Apr. 9, 2020

(51) Int. Cl.
| | |
|---|---|
| *A61B 17/12* | (2006.01) |
| *A61M 29/02* | (2006.01) |
| *A61M 25/09* | (2006.01) |
| *A61F 2/95* | (2013.01) |

(52) U.S. Cl.
CPC .. *A61B 17/12136* (2013.01); *A61B 17/12031* (2013.01); *A61B 17/12109* (2013.01); *A61M 25/09041* (2013.01); *A61M 29/02* (2013.01); *A61F 2/95* (2013.01)

(58) Field of Classification Search
CPC ........ A61B 17/12136; A61B 17/12031; A61B 17/12109; A61B 2017/1139; A61B 2017/1107; A61M 29/00; A61M 29/02; A61F 2/95; A61F 2/958; A61F 2/962; A61F 2/966
See application file for complete search history.

(56) References Cited

U.S. PATENT DOCUMENTS

| | | | |
|---|---|---|---|
| 5,258,042 A | * | 11/1993 | Mehta ............. A61B 17/12022 600/36 |
| 6,099,548 A | | 8/2000 | Taheri |
| 6,206,868 B1 | | 3/2001 | Parodi |
| 6,524,300 B2 | | 2/2003 | Meglin |
| 6,723,116 B2 | | 4/2004 | Taheri |
| 7,374,561 B2 | | 5/2008 | Barbut |
| 8,372,108 B2 | | 2/2013 | Lashinski |
| 9,662,118 B2 | | 5/2017 | Chang |
| 10,470,797 B1 | | 11/2019 | Rai et al. |
| 2001/0044958 A1 | | 11/2001 | DeAngelo |
| 2002/0082592 A1 | * | 6/2002 | Lary ............. A61B 17/320725 606/15 |

(Continued)

OTHER PUBLICATIONS

Cleveland Clinic; Cerebral protection in TAVR: approval marks start of a new era; 10 pages; retrived from the internet (https://consultqd.clevelandclinic.org/cerebral-protection-in-tavr-approval-marks-start-of-a-new-era/) on Dec. 10, 2018.

(Continued)

*Primary Examiner* — Wade Miles
(74) *Attorney, Agent, or Firm* — Shay Glenn LLP

(57) ABSTRACT

Methods and devices for performing transjugular carotid flow reversal are provided. A flow reversal sheath is advanced through a transjugular carotid fistula. An occlusion balloon is inflated, causing carotid inflow to be diverted through the sheath and through a flow reversal region positioned in the jugular vein. After reversal of blood flow, a carotid intervention is performed.

21 Claims, 20 Drawing Sheets

(56) References Cited

U.S. PATENT DOCUMENTS

2008/0200946 A1 8/2008 Braun et al.
2018/0161551 A1 6/2018 Pillai
2020/0016381 A1* 1/2020 Calhoun .......... A61B 17/12136

OTHER PUBLICATIONS

Kwolek et al.; Results of the roadster multicenter trial of transcarotid stenting with dynamic flow reversal; Journal of Vascular Surgery; 62(5); pp. 1227-1234; Nov. 2015.
Medtronic; Cragg-McNamara valved infusion catheters; (Product Page); 9 pages; retrieved from the internet (https://www.medtronic.com/us-en/healthcare-professionals/products/cardiovascular/infusion-therapy-products/cragg-mcnamara-catheters.html); on Dec. 10, 2018.
Medtronic;Mo.Ma Ultra proximal cerebral protection device; (Product Page); 6 pages; retrived from the internet (https://www.medtronic.com/us-en/healthcare-professionals/products/cardiovascular/embolic-protection-devices/mo-ma.html) on Dec. 10, 2018.
Merit Medical; Mistique infusion catheters; 13 pages retrieved from the internet (https://www.merit.com/peripheral-intervention/intervention/therapeutic-infusion-systems/mistique-infusion-catheters/) on Dec. 10, 2018.
Parodi et al.; Proximal occlusion and flow reversal: The ideal cerebral protection method during carotid artery stenting; Endovascular today; pp. 67-71; 4 pages; retrived Dec. 10, 2018 from the internet (https://evtoday.com/pdfs/EVT1106_07.pdf); Nov. 2006.
Silkroad Medical; Enroute: Transcarotid neuroprotection and stent system; 4 pages; retrived from the internet (https://silkroadmed.com/enroute-transcarotid-neuroprotection-system/) on Dec. 10, 2018.
Weber et al.; Proximal protection devices and flow reversal for embolic protection; Vas. Dis. Manage.; 11; pp. E21-26; Jan. 2014.
Pillai; U.S. Appl. No. 16/714,424 entitled "Devices and methods using precutaneous transjugular carotid flow reversal," filed Dec. 13, 2019.

* cited by examiner

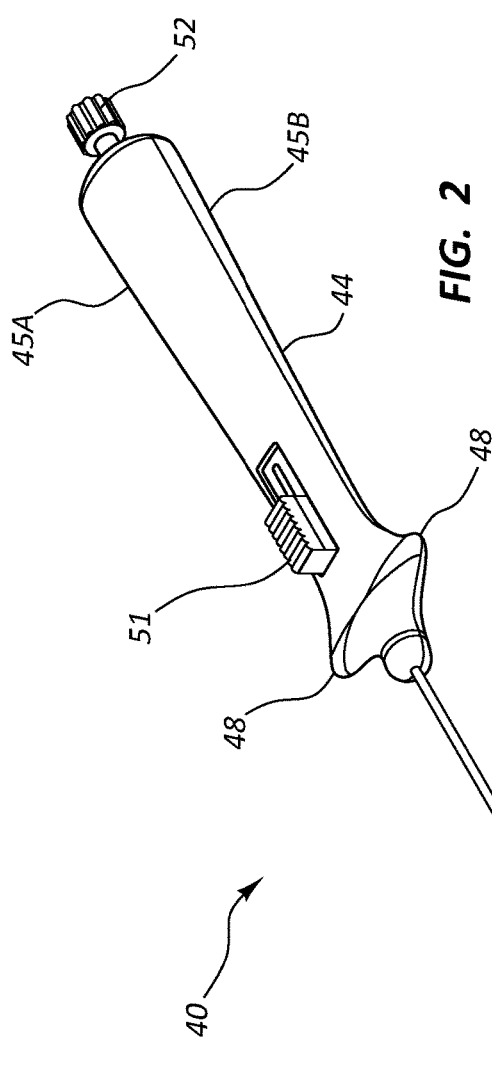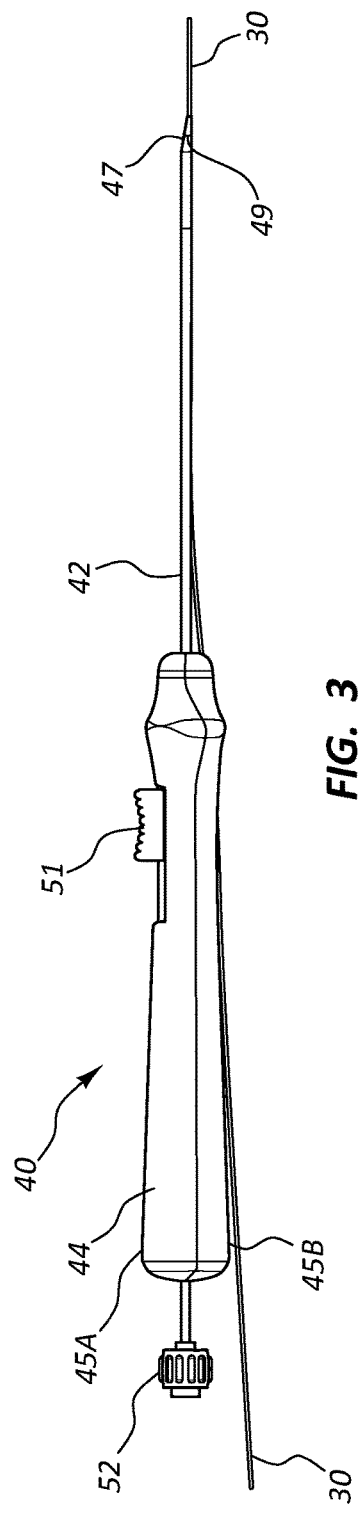

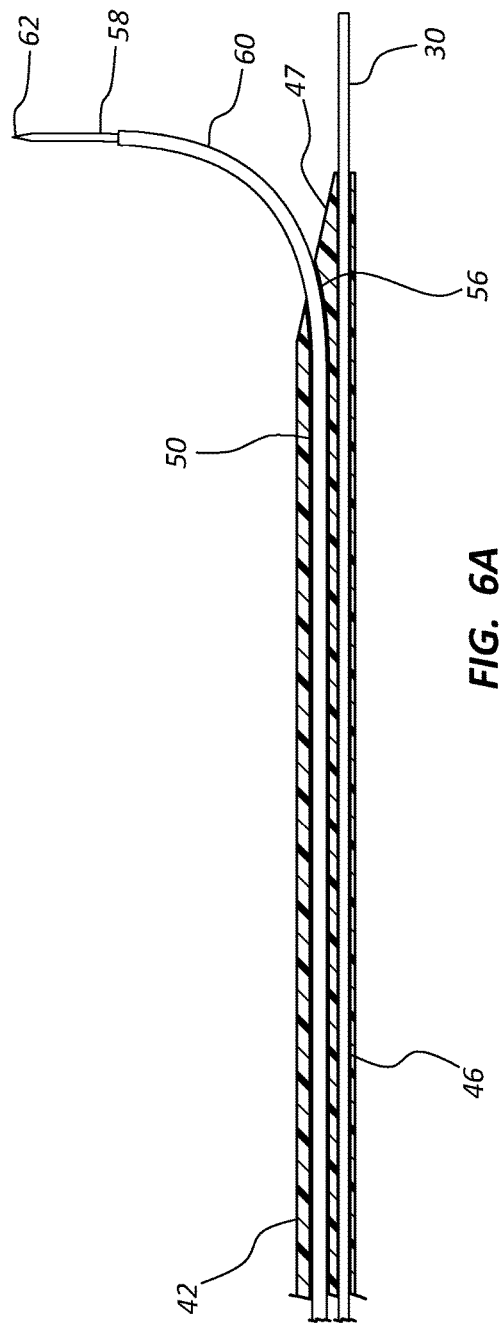
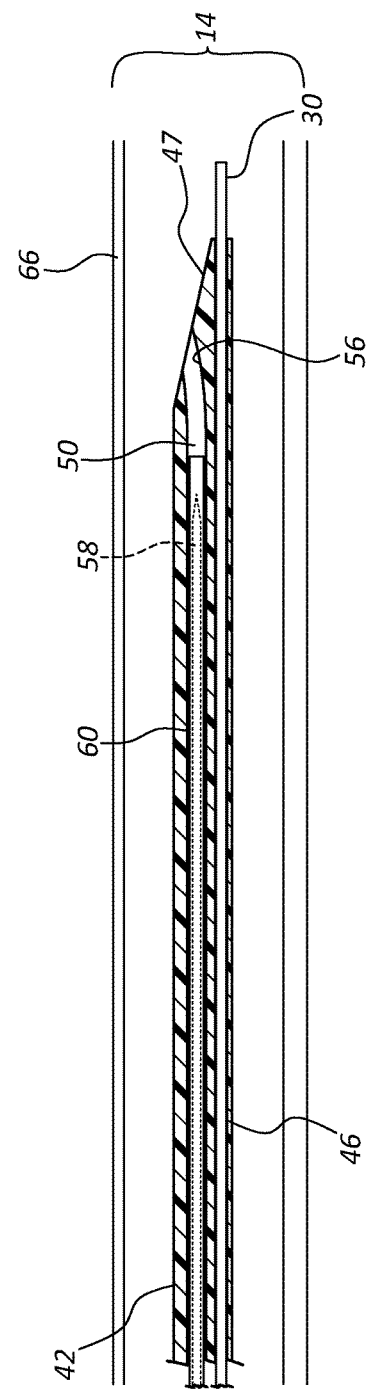
FIG. 6A
FIG. 6B

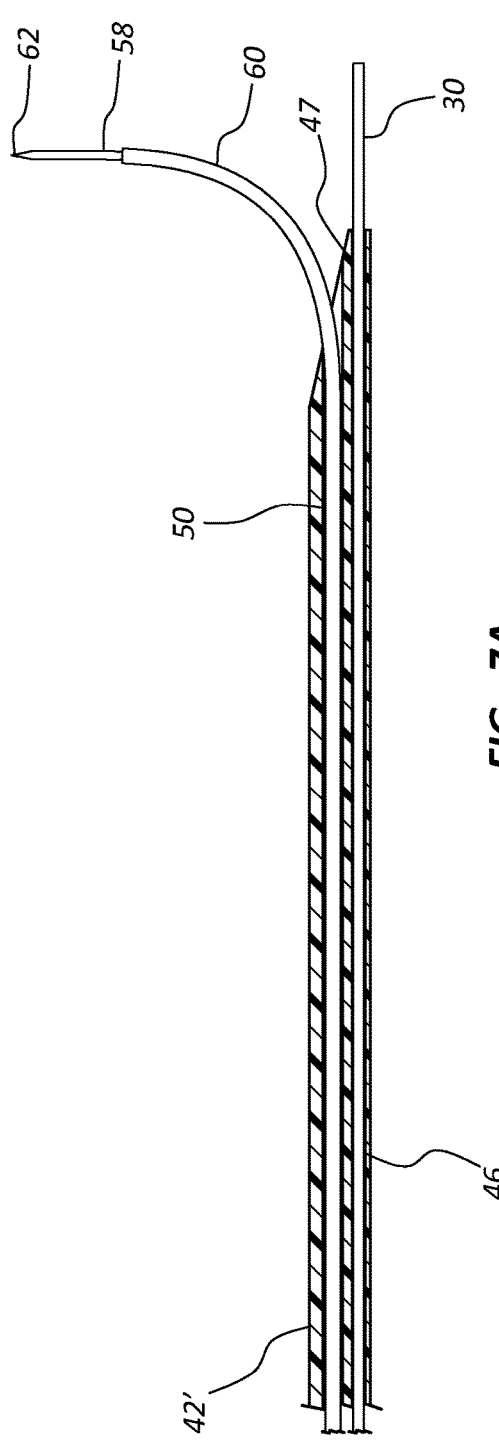
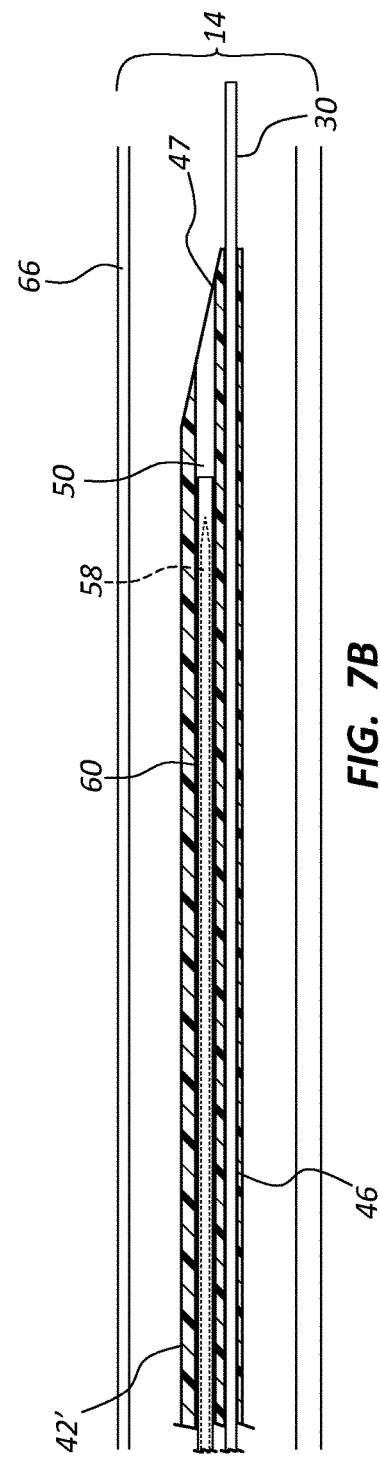
FIG. 7A
FIG. 7B

CAROTID ARTERY EMBOLIC PROTECTION METHOD USING PERCUTANEOUS TRANSJUGULAR CAROTID FLOW REVERSAL

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Embolization to the brain and subsequent stroke is a risk inherent in carotid artery interventions, such as carotid artery stenting procedures. There exist various methods and mechanisms to reduce this risk.

An embolic protection device may be placed in the carotid artery to trap embolic material dislodged during carotid angioplasty, carotid stenting or transaortic valve interventions to prevent the embolic material from entering the cerebral vasculature. Examples of current embolic protection devices for the carotid artery include the Medtronic SpiderFx® device, the Abbott Emboshield® Nav6 device, and the Boston Scientific FilterWire EZ™ device. Such devices are typically delivered to the carotid artery via a catheter inserted into the femoral artery and advanced into the aorta. The embolic protection device and its delivery guidewire are typically left in place during the interventional procedure.

Another method of reducing embolization risk is to reverse flow in the carotid artery during the carotid artery intervention. Systems like Silk Road Medical's ENROUTE® Transcarotid Neuroprotection and Stent System reverse blood flow during carotid stent placement by connecting the carotid artery to an external system that will reverse the flow of blood away from the brain. The blood is filtered and returned to the body through the femoral vein in a patient's thigh. The Parodi antiembolism system reverses flow by externally connecting the carotid artery to the jugular vein. There does not exist a system or device for reversing flow from the carotid artery to the jugular vein internally.

SUMMARY

In a first aspect, a flow reversal sheath for reversing flow in the carotid artery is provided. The sheath comprises an inner lumen; an occlusion balloon positioned proximal to a distal end of the flow reversal sheath and configured to block flow in the carotid artery; and a flow reversal region positioned proximal to the occlusion balloon and comprising a plurality of holes in a sidewall of the flow reversal sheath, the flow reversal region configured to be positioned in the jugular vein.

In some embodiments, the occlusion balloon is positioned about 1 cm from the distal end of the sheath. The balloon can comprise a diameter of about 10-12 mm. In some embodiments, the sheath has a diameter of about 10 F. The flow reversal region can be positioned about 5 cm from the distal end of the flow reversal sheath. In some embodiments, the flow reversal region comprises a length of about 10 cm. The inner lumen can be rigid. In some embodiments, the inner lumen is impervious to fluid. The sheath can comprise a hemostatic valve at a proximal end of the sheath. In some embodiments, the sheath comprises an inflation lumen.

In another aspect, a system for reversing flow in the carotid artery is provided. The system comprises a guidewire for advancing to an opening between the jugular vein and carotid artery; a dilator for enlarging the opening between the jugular vein and the carotid artery; and a flow reversal sheath comprising an inner lumen, an occlusion balloon positioned proximal to a distal end of the flow reversal sheath and configured to block flow in the carotid artery; a plurality of holes in a sidewall of the flow reversal sheath and positioned in a flow reversal region positioned proximal to the occlusion balloon, the flow reversal region configured to be positioned in the jugular vein.

In some embodiments, the system comprises an inner obturator configured to be positioned within the inner lumen. The system can comprise a hollow outer obturator configured to be positioned in the flow reversal sheath around the inner lumen.

In yet another aspect, a method for reversing flow in the carotid artery is provided. The method comprises advancing a guidewire through an opening between the jugular vein and the carotid artery; dilating the opening; advancing a flow reversal sheath through the dilated opening so that a distal end of the flow reversal sheath is positioned in the carotid artery; and inflating a balloon positioned proximal to the distal end of the flow reversal sheath to reverse flow in the carotid artery and causing blood to flow from the carotid artery through a flow reversal region of the flow reversal sheath configured to be positioned in the jugular vein.

In some embodiments, the method comprises forming an opening between the jugular vein and the carotid artery. The method can comprise advancing a working sheath through an inner lumen of the flow reversal sheath. In some embodiments, the method comprises performing a carotid intervention after reversal of blood flow in the carotid artery. The method can comprise performing balloon tamponade of the opening. In some embodiments, the method comprises implanting a stent in the jugular vein across the opening. The method can comprise dilating the opening comprises dilating the opening to about 3.2 mm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 illustrates a perspective view of a transvascular access device accordingly to an embodiment.

FIG. 3 illustrates a side view of the device of FIG. 2 coupled to a guidewire.

FIG. 6A illustrates a cross-sectional schematic view of a vascular catheter of the device of FIG. 2 in a configuration with the stylet deployed.

FIG. 6B illustrates a cross-sectional schematic view of the vascular catheter of the device of FIG. 2, in a retracted configuration with the stylet retracted, being advanced over a guidewire in a vessel, such as a vein.

FIG. 7A illustrates a cross-sectional schematic view of a device in accordance with an embodiment with the stylet deployed in an actuated configuration.

FIG. 7B illustrates a cross-sectional schematic view of a device in accordance with an embodiment, in a retracted configuration with the stylet retracted, being advanced over a guidewire in a vessel, such as a vein.

DETAILED DESCRIPTION

Described herein are methods and systems for creating trans-jugular flow reversal in the carotid arteries. The flow reversal can be performed prior to performing a protected carotid intervention. These methods and systems provide a minimally invasive way to prevent embolic events during carotid intervention. The flow reversal method described herein differs from existing flow reversal systems currently available at least because the rerouting of the blood from the carotid access occurs internally, within the patient's body. Accessing the carotid artery and reversing carotid flow through the jugular vein eliminates the need for surgical exposure of the carotid artery, greatly reducing the risks of the procedure. In addition, eliminating the need for surgical exposure makes the procedure interventional, allowing an interventional cardiologist, radiologist, or neurologist, instead of a surgeon, to perform the procedure. The flow reversal method described herein also differs from other currently available systems that use suction to initiate flow reversal in the carotid artery. Allowing flow from a higher pressure region, like the carotid artery, to a lower pressure area, like the jugular vein, can provide less trauma to the carotid artery than a procedure using suction.

Access to the carotid artery can be provided through the jugular vein. US Patent Publ. No. 2018/0161551 describes methods and devices for trans-jugular access of the carotid artery. This patent publication does not describe using the trans-jugular access to reverse flow in the carotid artery.

Figure 1A:
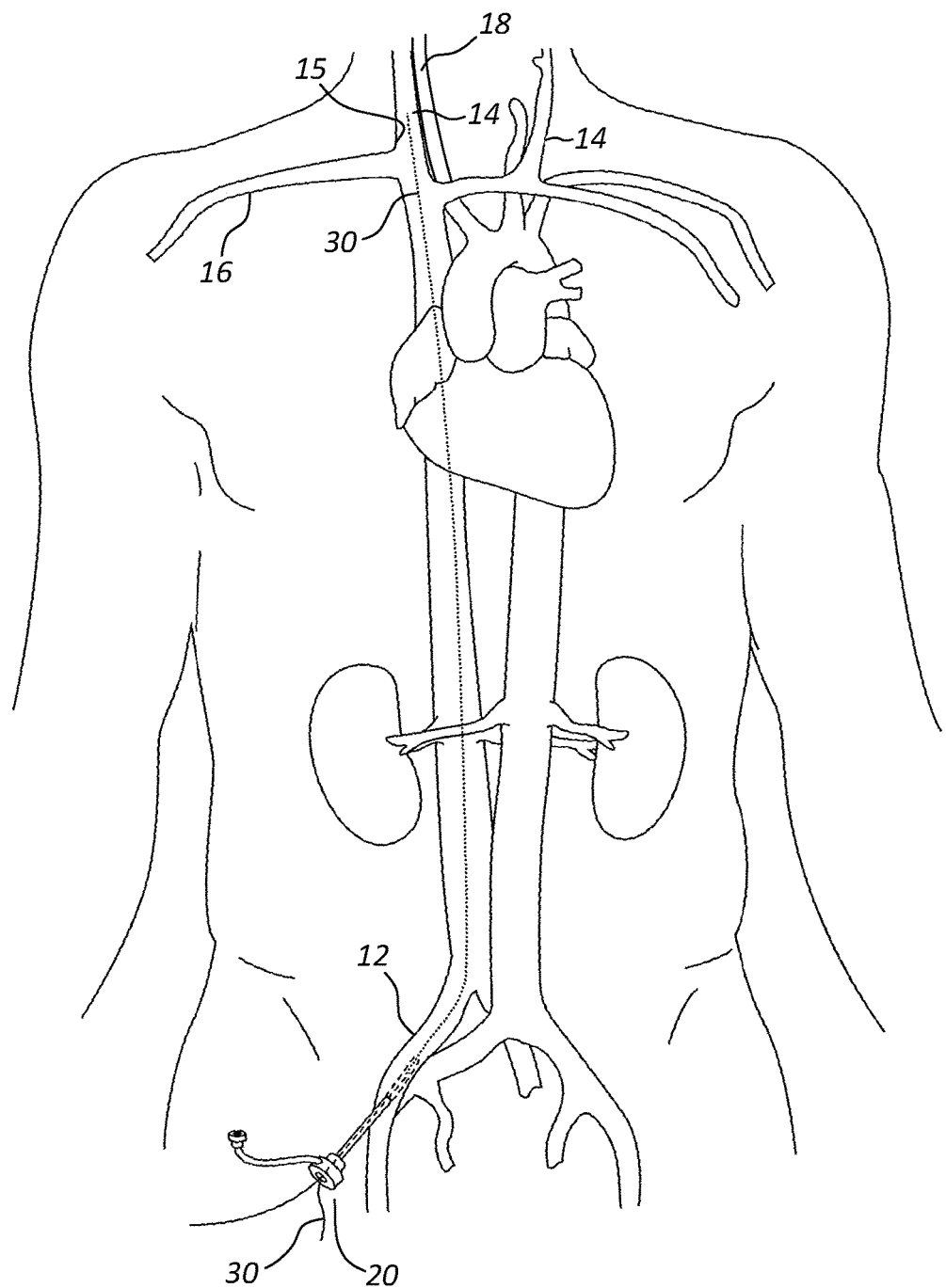
FIG. 1A is a schematic drawing illustrating the insertion of a guidewire extending from a patient's femoral vein to the jugular vein.
Figure 1B:
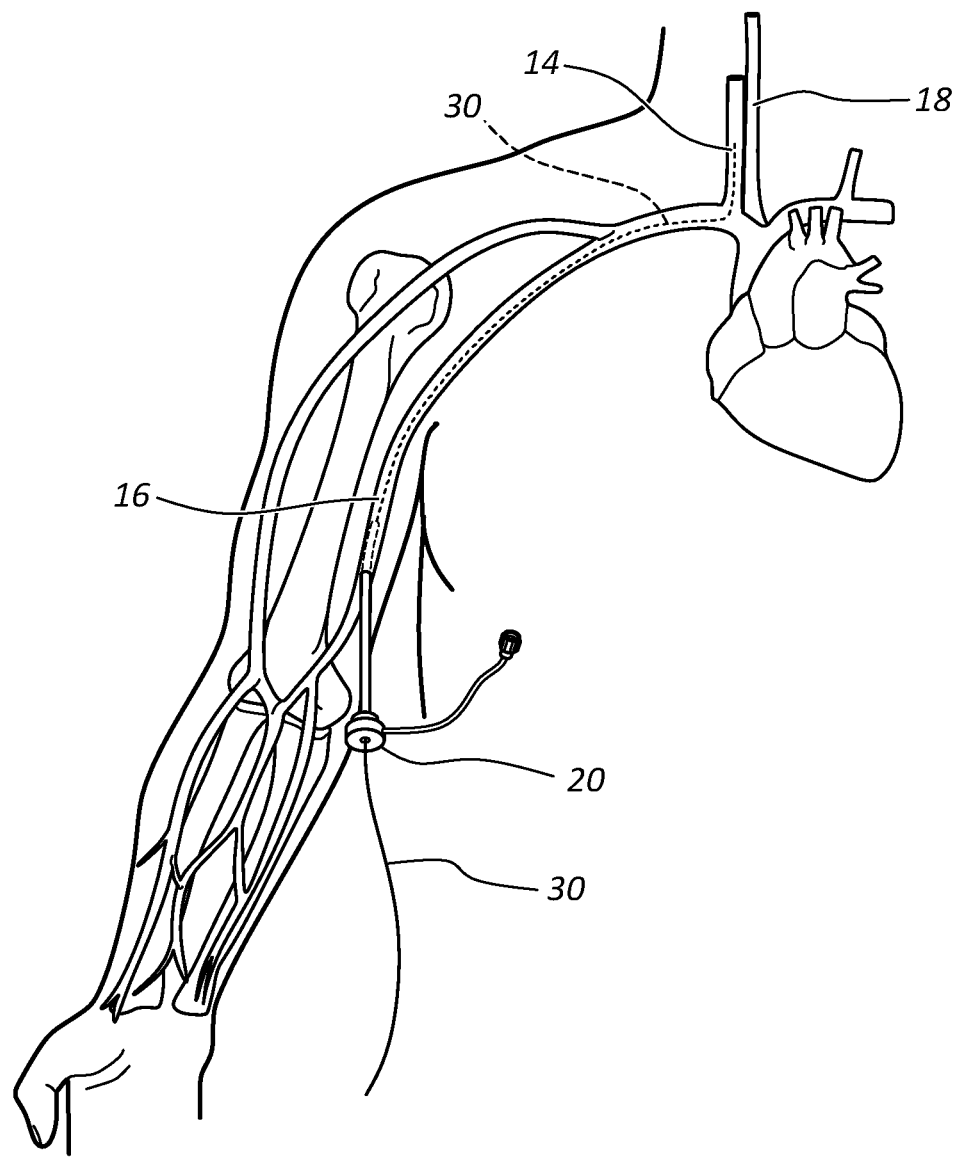
FIG. 1B is a schematic drawing illustrating the insertion of a guidewire extending from a patient's vein in their arm to the jugular vein.

As described in US Patent Publ. No. 2018/0161551, a first step in the method is to advance a guidewire into the jugular vein in a manner known in the art. Access to the jugular vein may be achieved via a femoral vein, such as by the Modified Seldinger Technique, as shown in FIG. 1. A general use guidewire 30 (such as a guidewire measuring about 0.0035 inches in diameter) may be passed through a vascular sheath 20 and positioned in a right or left jugular vein 14 of the patient via the inferior vena cava. The guidewire 30 may ultimately be positioned in the vicinity of a desired access point to a carotid artery 18. The desired access point may be located at any point along the jugular vein 14 where the jugular vein also runs along the carotid artery 18. For example, the desired access point may be just below the bifurcation of the carotid artery 18 into the internal carotid artery 19 and the external carotid artery 17. In this manner, a medical practitioner may be able to access the carotid artery 18 without having to do an open surgical procedure or to advance percutaneously from the patient's femoral artery and past the patient's aortic arch.

Alternatively, the remote entry point may be a vein within the patient's arm (e.g., brachial vein, basilic vein, cephalic vein, etc.).

The present invention may employ the access device described in US Patent Publ. No. 2018/0161551. As shown in FIGS. 2-6B, access device 40 includes a vascular catheter 42 extending distally from a handle 44. The length and diameter of the vascular catheter 42 depends on the distance between a remote entry point and the desired access point to the carotid artery 18. For example, if the remote entry point is the femoral vein 12, the vascular catheter 42 may have a length of about 1 meter and may have a diameter of around 7 french (0.092 inches). Alternatively, if the remote entry point is a vein within the patient's arm (e.g., brachial vein, basilic vein, cephalic vein, etc.), the vascular catheter 42 may have a length of about half a meter and a diameter around 7 french.

The vascular catheter 42 may comprise a catheter tip 47 at the distal end of the vascular catheter 42. The catheter tip 47 may be tapered, beveled, conical or comprise other shapes or structures. The catheter tip 47 in FIG. 3 is illustrated as conical. In some embodiments, the vascular catheter 42 may have a guidewire lumen 46, as illustrated in FIGS. 2-6B. The guidewire lumen 46 may be configured to be a rapid exchange (RX) guidewire lumen for receiving the guidewire 30. In embodiments in which the remote entry point is the femoral vein 12 and the desired access point is the carotid artery 18, the guidewire 30 may be a 0.035 inch guidewire. In some embodiments the guidewire 30 is advanced through the handle 44 of the access device 40. In some embodiments the guidewire 30 may be introduced into the guidewire lumen 46 using an introducer kit (not shown). The guidewire 30 may be positioned adjacent to the desired access point in the patient's jugular vein 14. The vascular catheter 42 may be advanced over the guidewire 30 before or after the guidewire 30 is positioned adjacent to the desired access point in the jugular vein 14.

Figure 4A:
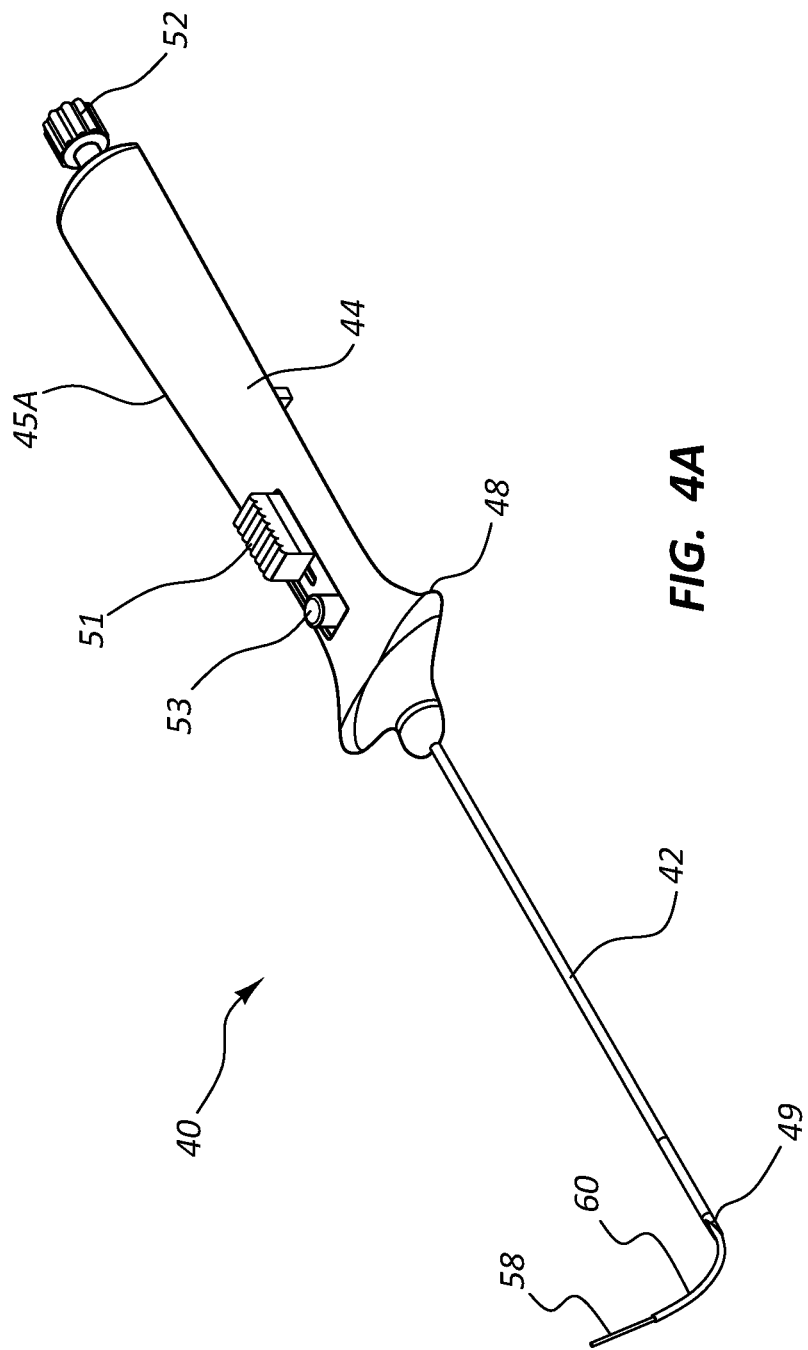
FIG. 4A illustrates a perspective view of the device of FIG. 2.
Figure 4B:
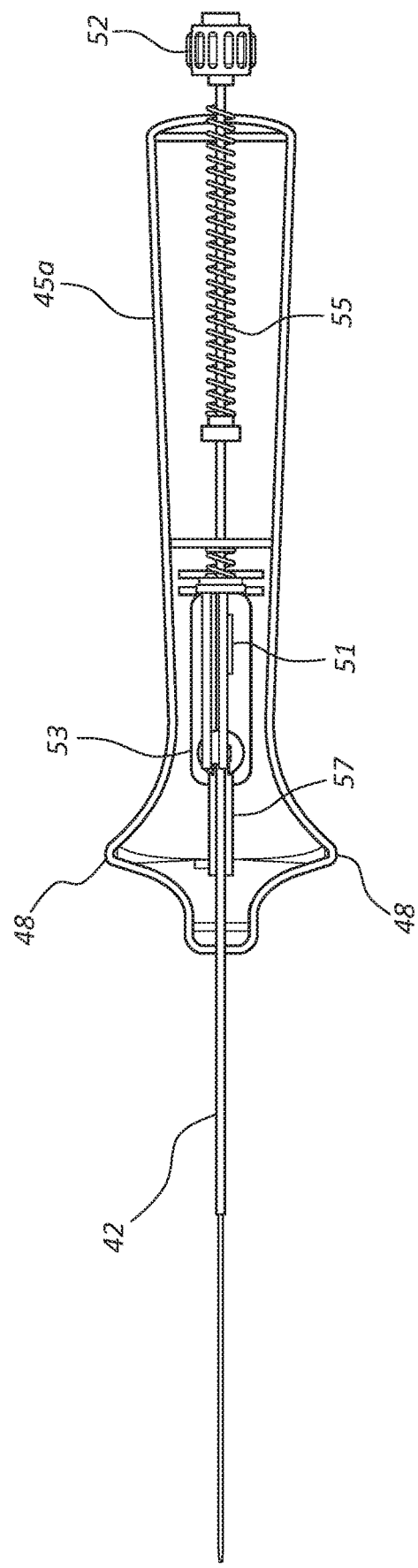
FIG. 4B illustrates a bottom view of the device of FIG. 2 with a top portion removed to expose interior components.
Figure 4C:
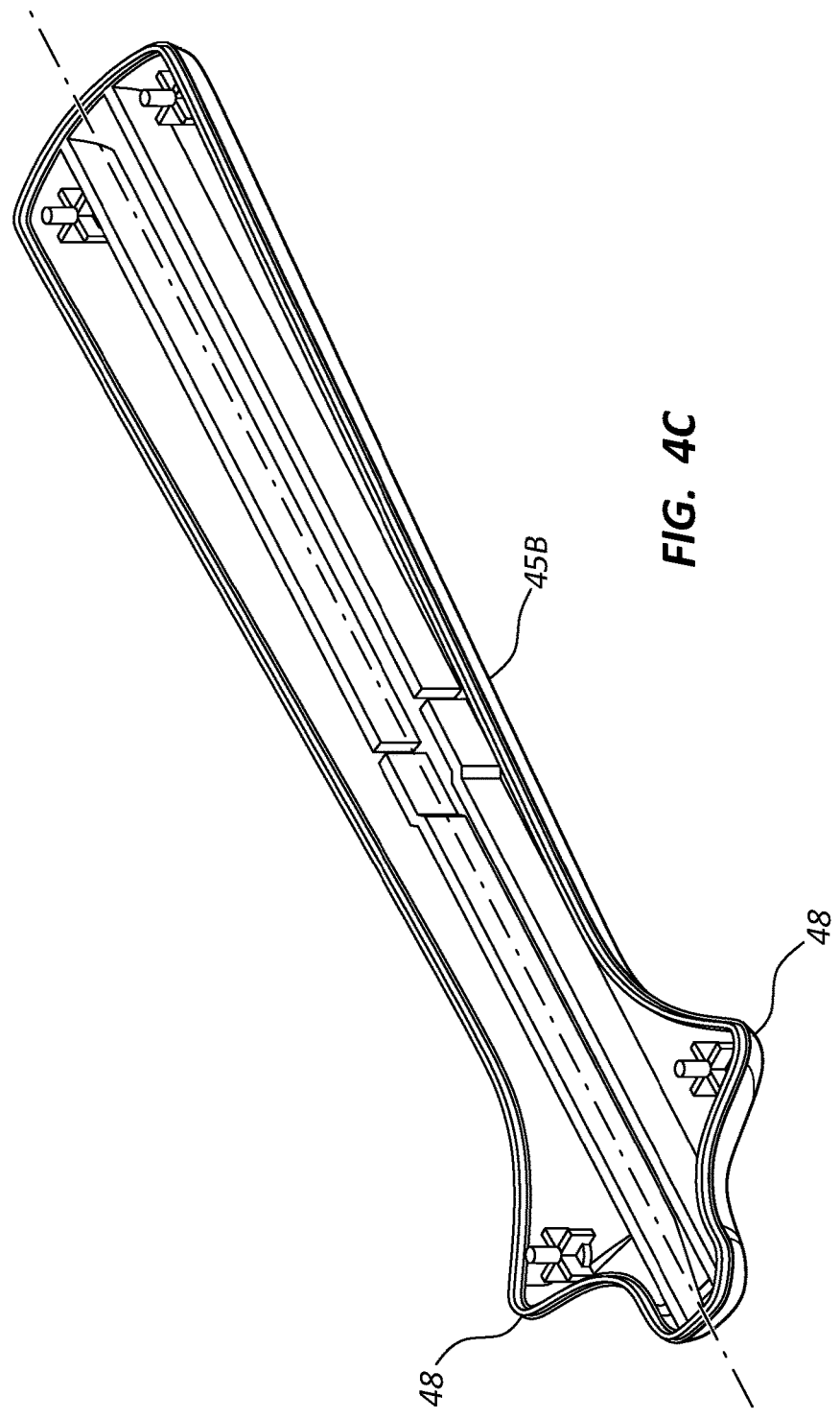
FIG. 4C illustrates a perspective view a bottom portion of the housing of the device of FIG. 2, with other components removed.

The handle 44 may include a top portion 45A and a bottom portion 45B. FIG. 4A is a top perspective view of the top portion 45A of the handle 44 along with other components. FIG. 4B is a bottom view of the top portion 45A of the handle 44, along with other components of the device, with the bottom portion 45B removed to expose internal components. FIG. 4C illustrates a bottom portion 45B of the handle 44. The top portion 45A and the bottom portion 45B may engage to from the handle 44. The handle 44 also includes wings 48 on opposing sides of the handle 44. The wings 48 may be used to apply a distal force to the vascular catheter 42 from the handle 44.

FIGS. 6A-B show a distal portion of one embodiment of the vascular catheter 42. In addition to the guidewire lumen 46, the device 40 may have a stylet lumen 50 extending from the handle 44 to an opening toward the distal end of the vascular catheter 42. In this embodiment, the stylet lumen 50 curves at its distal end to form a camming surface 56, as illustrated in FIGS. 6A and 6B. The camming surface 56 may provide additional structural support to a guide tube or a cover tube 60 when it is in an advanced position.

A stylet 58 may be slideably disposed within cover tube 60. The stylet 58 (formed, e.g., from Nitinol with a diameter of 0.014 inches) enclosed by the cover tube 60 (such as a 0.025 inch diameter Nitinol hypotube) extends from an actuator 51, 52, and 53, in the handle 44 toward the distal end of the device 40. In some embodiments the cover tube 60 has a preformed curved or deflected tip at its distal end. For example, the performed curve may be between 30° and 60° of the longitudinal axis of vascular catheter 42. The optional camming surface 56 may promote the curvature of the cover tube 60.

Stylet 58 may have a sharp distal point 62 adapted to penetrate tissue, such as blood vessels, muscle, and skin. The sharp distal point 62 may be part of a tip designed to have various dimensions and shapes. In some embodiments, the tip 62 may be faceted. For example, the tip 62 may include three flat surfaces that intersect to form a sharp distal point. In some embodiments, tip 62 may be a conical tip. The conical tip may form an angle of about 10° with the shaft of the stylet 58.

In an alternative embodiment shown in FIGS. 7A-B, the optional camming surface of the prior embodiment is omitted, and the stylet lumen 50 may be substantially cylindrical. Other elements of this embodiment are the same as in the embodiment of FIGS. 6A-B.

Figure 8:
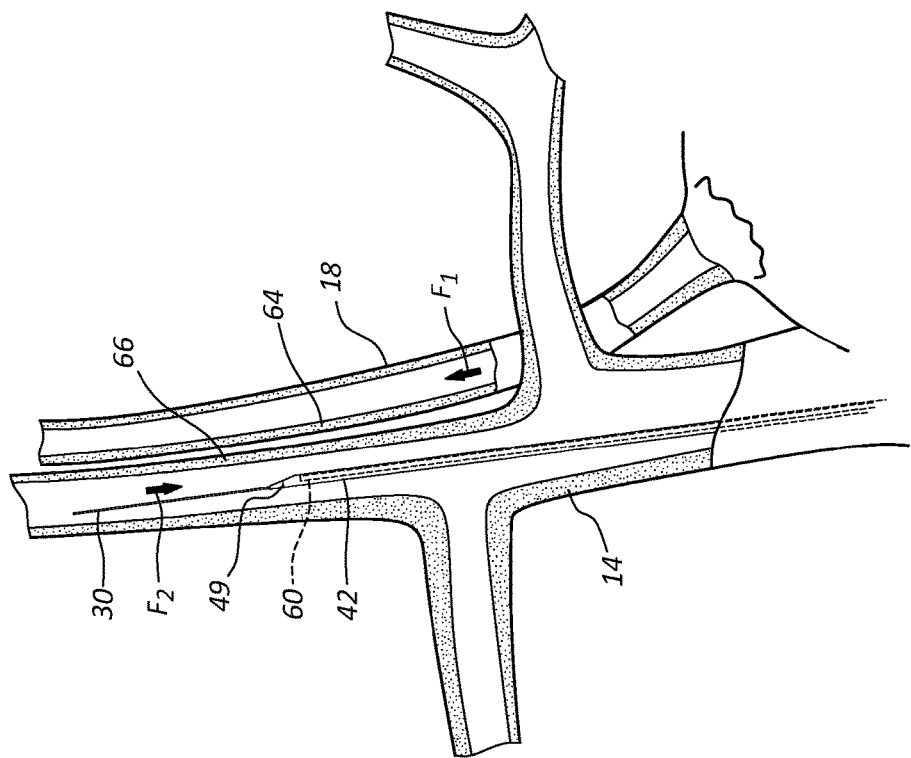
FIG. 8 illustrates a schematic view of the device of FIG. 2 in a retracted configuration, with a vascular catheter in the jugular vein close to an access point for the carotid artery.

To gain access of the carotid artery 18, vascular catheter 40 may be inserted into the femoral vein 12 over the guidewire 30 (with the guidewire disposed as shown in FIG. 1) and may be advanced adjacent to the desired access point in the jugular vein 14 under fluoroscopic guidance. During this advancement, the stylet 58 and cover tube 60 may be in a retracted configuration, as illustrated in FIG. 8. The distal opening of the stylet lumen 50 may then be oriented toward the desired carotid artery access point in the vein wall 66.

Figure 9:
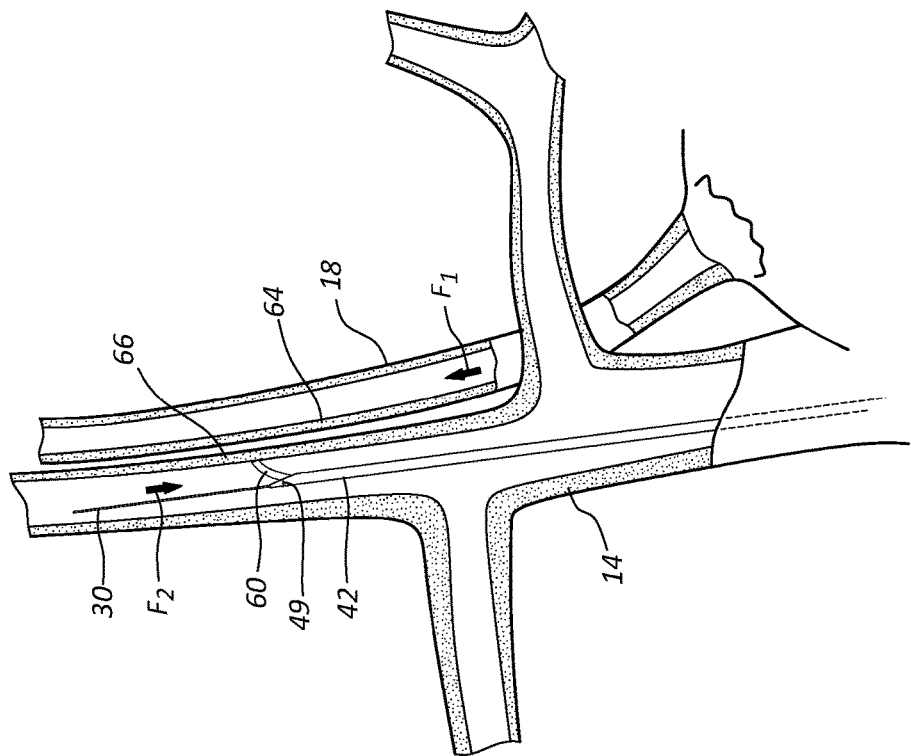
FIG. 9 illustrates a schematic view of the device of FIG. 2 in a primed configuration with the stylet cover tube advanced to a desired access point for the carotid artery.
Figure 11:
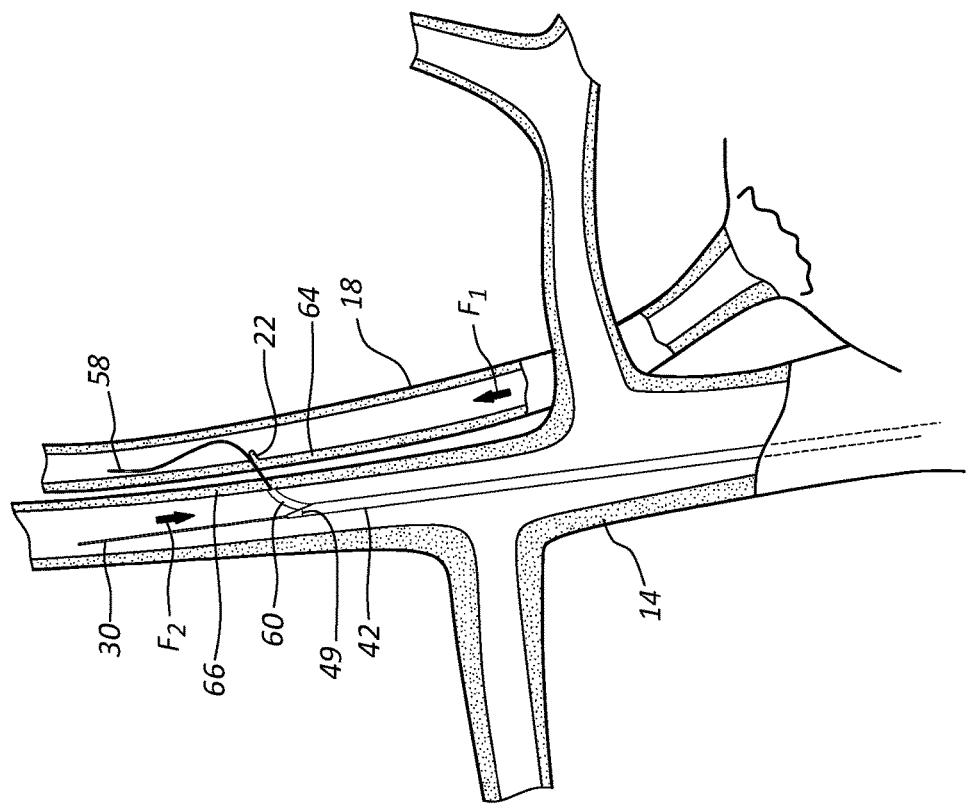
FIG. 11 illustrates a schematic view of the device of FIG. 2 with an access catheter advanced over the stylet.
Figure 10:
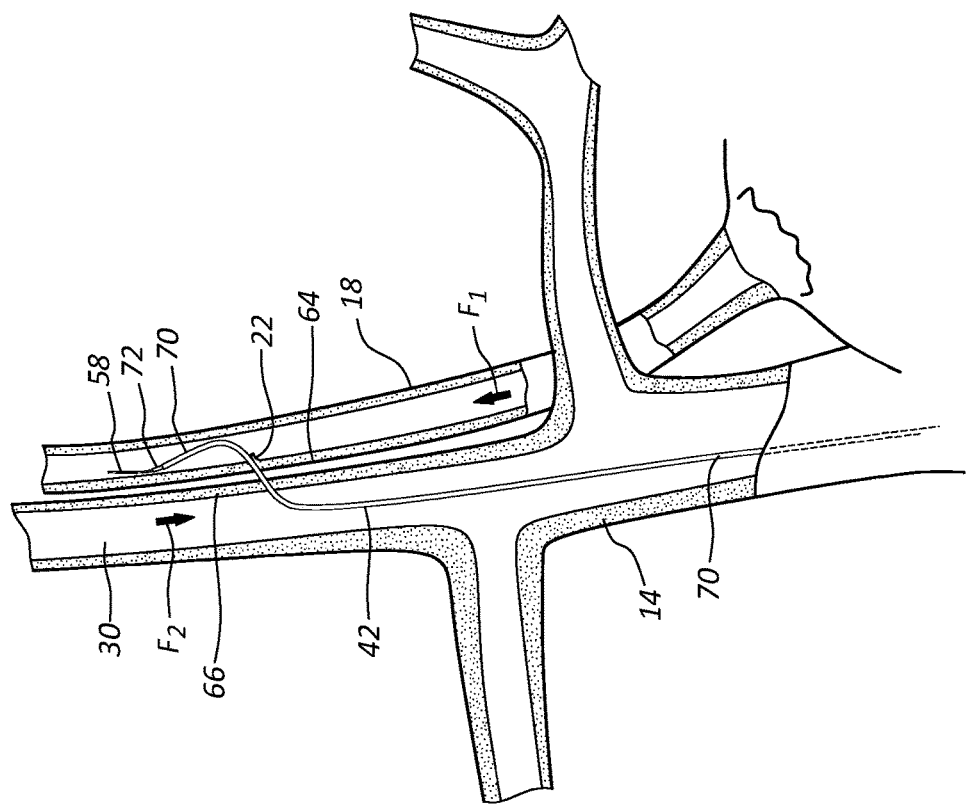
FIG. 10 illustrates a schematic view of the device of FIG. 2 in an actuated configuration with the stylet advanced through the vessel wall of the jugular vein and into the carotid artery.

The arrows ($F_1$ and $F_2$) in FIGS. 8-11 illustrate the direction of blood flow in the jugular vein 14 and the carotid artery 18. The blood in the carotid artery 18 flows away from the heart in direction $F_1$ and the blood flow in the jugular vein 14 flows toward to heart in direction $F_2$. In some embodiments the catheter tip 47 may include a radiopaque marker 49 visible under the fluoroscopy as illustrated in FIGS. 8-10. The radiopaque marker 49 may be embedded in the catheter tip 47. The radiopaque marker 49 is illustrated as a ring in FIGS. 9 and 10; however, other shapes and geometries may be used. In some embodiments the shape of the radiopaque marker 49 may be selected to facilitate fluoroscopic identification of the location and orientation of the catheter tip 47. Examples of radiopaque marker materials include gold, platinum, platinum-iridium, and other biocompatible radiopaque materials.

The cover tube 60 may be advanced out of opening into an primed configuration by moving a slide button 51 proximally in handle 44, at which point the cover tube 60 assumes its curved shape, as shown in FIGS. 5A, 6A, 7A and 9. In some embodiments, moving the slide button 51 proximally in handle 44 pushes the cover tube distally from the vascular catheter 42. In some embodiments moving the slide button 51 proximally in the handle 44 moves the catheter proximally to expose the distal end of the cover tube 60. As illustrated in FIGS. 4A and 4B, the slide button 51 may engage with and be operatively connected to the vascular catheter 42 with catheter slide 57. In some embodiments, the cover tube 60 is advanced until its distal end is adjacent to the vein wall 66 at the desired carotid artery access point. In some embodiments the cover tube 60 advances until its distal end abuts the vein wall 66 at the desired carotid artery access point. The stylet 58 remains in cover tube 60 in the primed configuration.

The orientation of the extended cover tube 60 may be determined based on the orientation of the handle 44. The slide button 51 engages with the top portion 45A of the handle 44. In the illustrated embodiment, the slide button 51 is disposed substantially perpendicular to a plane defined by the opposing wings 48 that extends along a length of the handle 44, e.g., the plane defined by the curve where the top portion 45A of the handle 44 contacts the bottom portion 45B of the handle 44. The cover tube 60 extends upwards from the stylet lumen 50 and is also substantially perpendicular to the plane defined by the opposing wings 48 extending along a length of the handle 44. The positioning and orientation of the cover tube 60 after it has been advanced may also be visually verified by, for example, using fluoroscopy prior to deploying the stylet 58. The stylet actuator is loaded by pulling proximally on a spring load mechanism 52 in the handle 44, as illustrated in FIG. 5A.

Figure 5A:
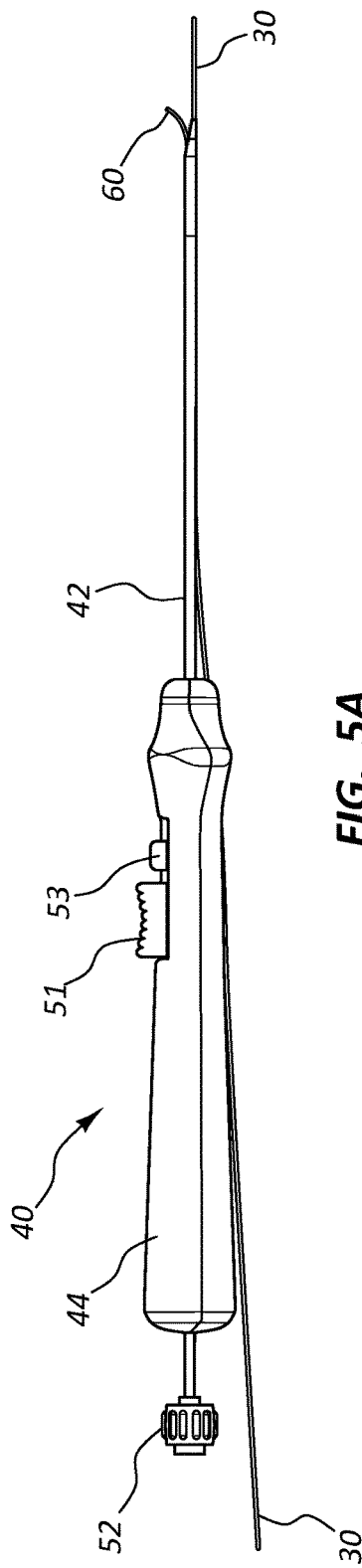
FIG. 5A is a side view of the device of FIG. 2 in a primed configuration with the stylet cover tube advanced and the stylet actuator loaded.
Figure 5B:
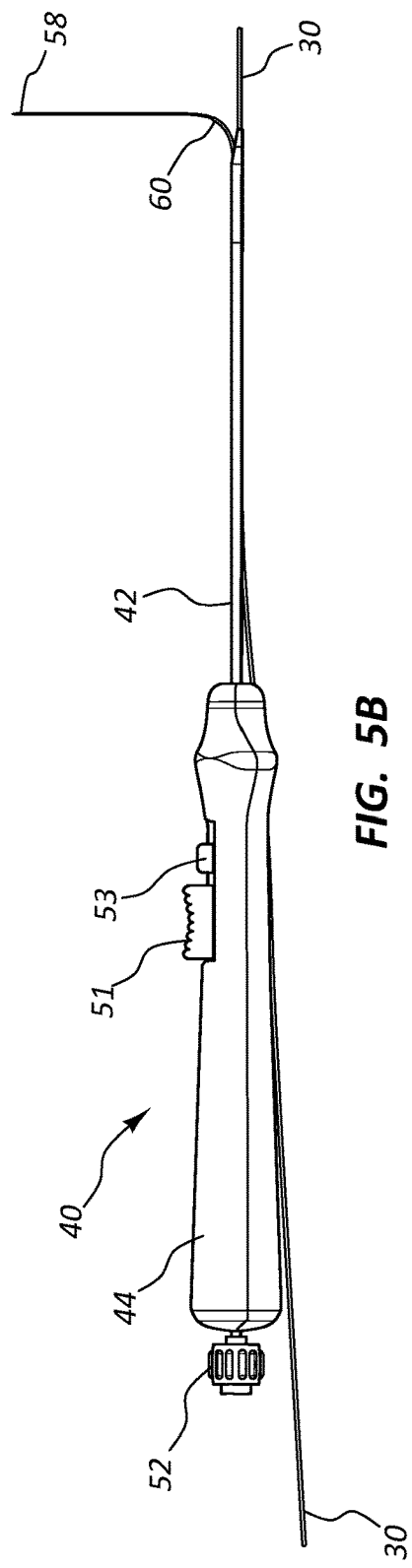
FIG. 5B illustrates a side view of the device of FIG. 2 in an actuated configuration with the stylet deployed.

When the slide button 51 is in its proximal position, as illustrated in FIG. 5A, a stylet release button 53 is exposed. Depressing release button 53 advances the stylet 58 distally under the action of a spring 55 to an actuated configuration, as illustrated in FIGS. 5B, 6A, 7A, and 10. The sharp distal tip penetrates the vein wall 66 of the jugular vein 14 and the artery wall 64 of the carotid artery 18, as illustrated in FIG. 10. After the stylet 58 punctures the carotid artery 18, the blood flow $F_1$ of the carotid artery may push the stylet 58 downstream so that it does not damage or perforate the opposing artery wall of the carotid artery 18. The puncture of the artery wall 64 may create a flap 22. The distance traveled by the stylet 58 depends on the application. For example, when the stylet 58 is moving from the jugular vein wall to the carotid artery 18, the stylet 58 may move less than half a centimeter. In other embodiments, the stylet 50 may move more or less than this amount, including 0.25 centimeters or less and 1, 2, 3, 4, or more centimeters.

Figure 12:
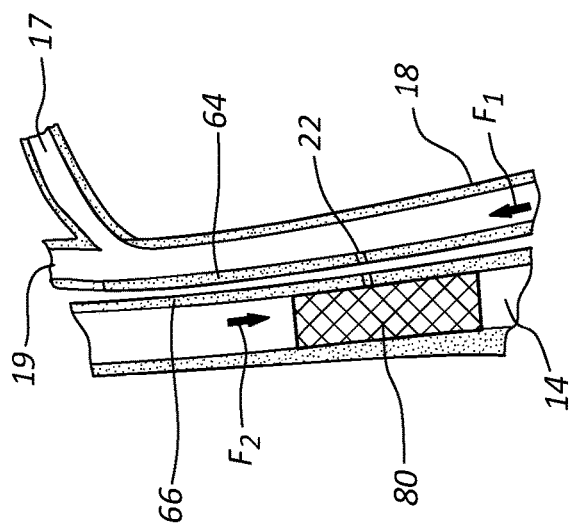
FIG. 12 illustrates a schematic view of a stent to close the opening between the jugular vein and the carotid artery.

After the procedure is concluded, the stylet 58, access catheter 70, and any treatment devices 72 may be withdrawn from the carotid artery 18 and the jugular vein 14. In addition, a closure device 80 may be introduced into the jugular vein 14 adjacent to the opening to close the opening between the jugular vein 14 and the carotid artery 18, as illustrated in FIG. 12. The closure device 80 may be a bioabsorbable, tightly meshed/woven venous stent 80. In addition, the opening in artery wall 64 of carotid artery 18 may be closed when the flap 22 is pushed back toward the opening by the blood flow $F_1$ in the carotid artery 18.

FIGS. 13-16 illustrate an alternative method to access the carotid artery 18 of a patient without open surgery and without passing through the aortic arch. The carotid artery 18 may be accessed directly from the patient's neck. For example, under B-mode ultrasound guidance (or fluoroscopy), a puncture needle 10 (e.g., 18 gauge for larger patients, 21 gauge for smaller patients) may be advanced through the skin 90 into the jugular vein 14 and then through the other side of the jugular vein 14 and into the carotid artery 18 at a point below the bifurcation of the carotid artery 18 into the internal carotid artery 19 and the external carotid artery 17. The puncture needle 10 thus creates an opening between the jugular vein 14 and the carotid artery 18 for fluid communication. The puncture needle 10 may also create a flap 22 in the artery wall of the carotid artery 18.

Figure 13:
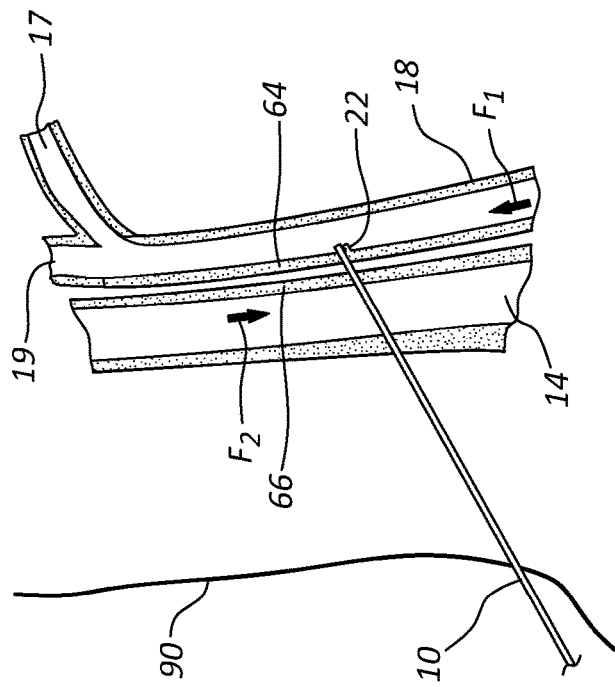
FIG. 13 illustrates a schematic view of a guidewire being introduced into the carotid artery via the puncture needle.

The puncture needle 10 may be inserted at a number of different orientations, for example, at an upward angle, a downward angel, etc. FIG. 13 illustrates the puncture needle 10 being inserted at an upward angle between 30° and 60° off the longitudinal axis of the jugular vein 14. The blood that flows out of the proximal end of the puncture needle 10 may indicate the location of the distal tip 21 of the puncture needle 10. Venous blood from the jugular vein 14 is darker and flows slowly and the higher pressure and more oxygenated arterial blood from the carotid artery 18 flows quicker and is redder than the blood from the jugular vein. This provides another indication to the practitioner that the puncture needle 10 has accessed the carotid artery 18.

Figure 14:
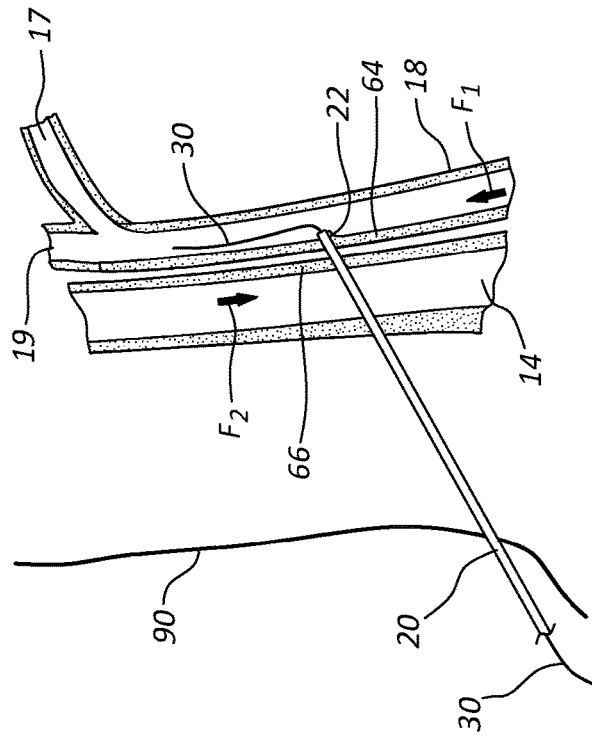
FIG. 14 illustrates a schematic view of a guidewire being introduced into the carotid artery via the puncture needle.
Figure 15:
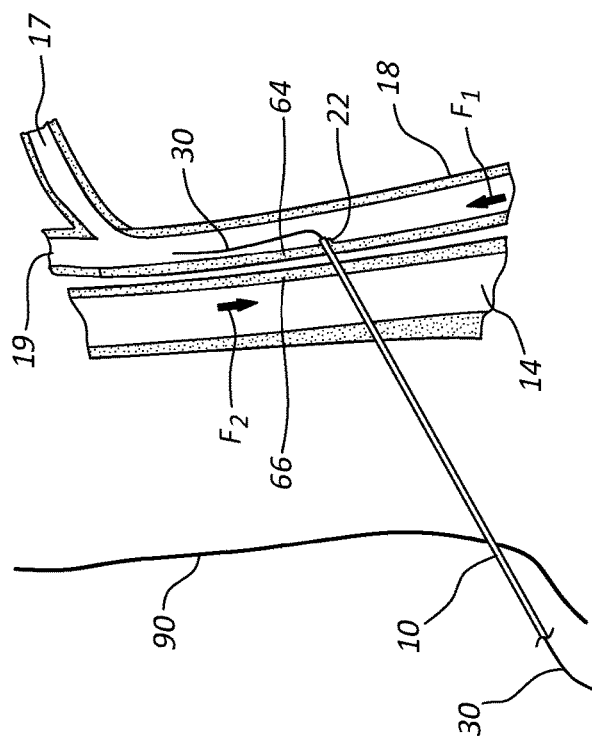
FIG. 15 illustrates a schematic view of an interventional sheath being advanced over the guidewire into the carotid artery.

After the distal tip 21 of the puncture needle 10 is in the carotid artery 18, a guidewire 30 may be advanced through the puncture needle 10 into the carotid artery 18, as illustrated in FIG. 14. After the guidewire 30 is advanced into the carotid artery 18, the puncture needle 10 may be removed and an interventional sheath 26 (e.g., with a diameter of 5 F or 6 F) may be advanced over the guidewire 30, as illustrated in FIG. 15. The interventional sheath 26 may provide access for a catheter or other treatment devices or tools to be advanced into the carotid artery 18 to perform a desired procedure, such as an angioplasty, plaque removal, treat aneurysms, etc. A number of different types of tools, such as angioplasty balloons, filters, stents, etc. may be used.

Figure 16:
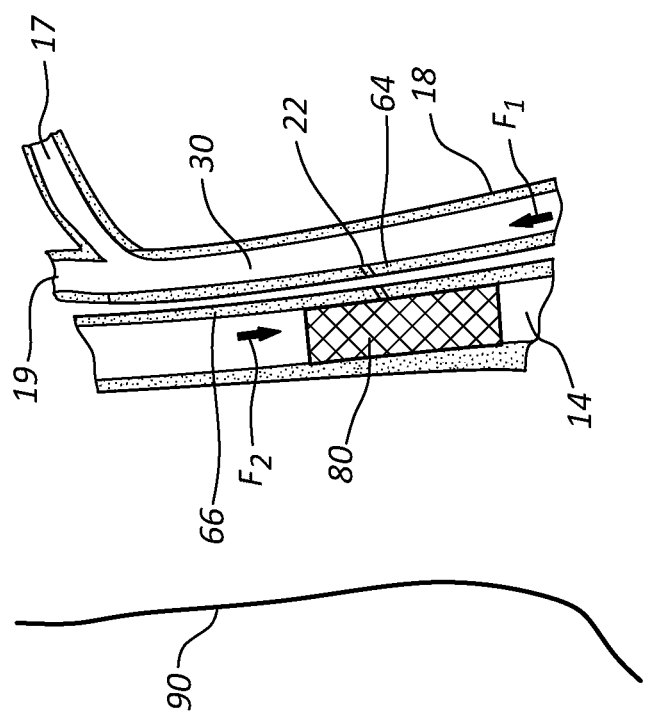
FIG. 16 illustrates a schematic view of a closure device being introduced into the jugular vein to close the opening between the jugular vein and the carotid artery.

After the completion of the carotid artery procedure, a closure device 80 may be introduced into the jugular vein 14 adjacent to the opening to close the opening between the jugular vein 14 and the carotid artery 18, as illustrated in FIG. 16. The closure device 80 may be a bioabsorbable, tightly meshed/woven venous stent. In addition, the opening in artery wall 64 of carotid artery 18 may be closed when the flap 22 is pushed back toward the opening by the blood flow $F_1$ in the carotid artery 18.

The closure device 80 may be inserted via the interventional sheath 26 (after it has been withdrawn from the carotid artery 18, but before withdrawing it from the internal jugular vein 14). Alternatively, the closure device 80 may be implanted using a separate catheter (not shown) that has been advanced from a remote entry point in the femoral vein 12 into the jugular vein 14.

Figure 17:
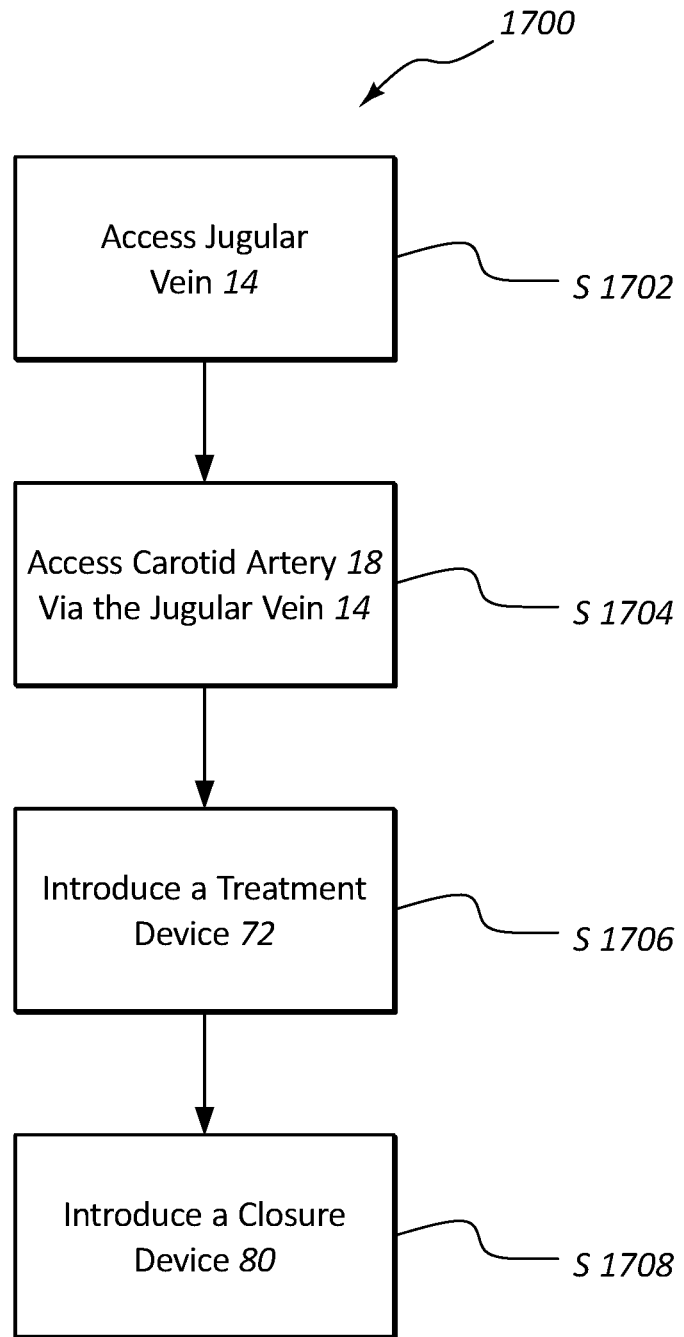
FIG. 17 illustrates a flowchart of a method of accessing a patient's carotid artery through their jugular vein.

FIG. 17 illustrates a flowchart of a method 1700 of accessing a patient's carotid artery 18 via their jugular vein 14, as previously discussed. In step 1702, the practitioner may access the patient's jugular vein 14 in a variety of different manners. For example, as previously discussed, the practitioner may access the jugular vein via a remote access point, such as a femoral vein 12 or a vein 16 in the patient's arm (e.g., brachial vein, basilic vein, cephalic vein, median antecubital, median antebrachial, etc.). Alternatively, the practitioner may access the jugular vein 14 directly by inserting a puncture needle 10 through the patient's neck.

In step 1704, the practitioner may access the carotid artery 18 via the jugular vein 14. For example, as previously discussed, the practitioner may access the carotid artery 18 by piercing the carotid artery 18 after piercing the jugular vein 14 with the puncture needle 10. Alternatively, the practitioner may advance a guidewire 30 and a vascular catheter 42 to the jugular vein 14 and pierce the carotid artery 18 with the stylet 58.

In step 1706, once the practitioner has gained access to the carotid artery 18, the practitioner may introduce or advance a treatment device for treating a medical condition via the carotid artery 18.

In step 1708, after the medical condition has been treated, the treatment device 72 may be removed and the practitioner may introduce a closure device 80 for closing the opening between the jugular vein 14 and the carotid artery 18.

Transjugular Carotid Flow Reversal

It will be appreciated that the above methods and devices are specific embodiments that can be used to create transjugular carotid access. Other tools and methods can also be used to create access to the carotid artery through the jugular vein, including, but not limited to, RF energy, cautery, and laser.

Figure 18:
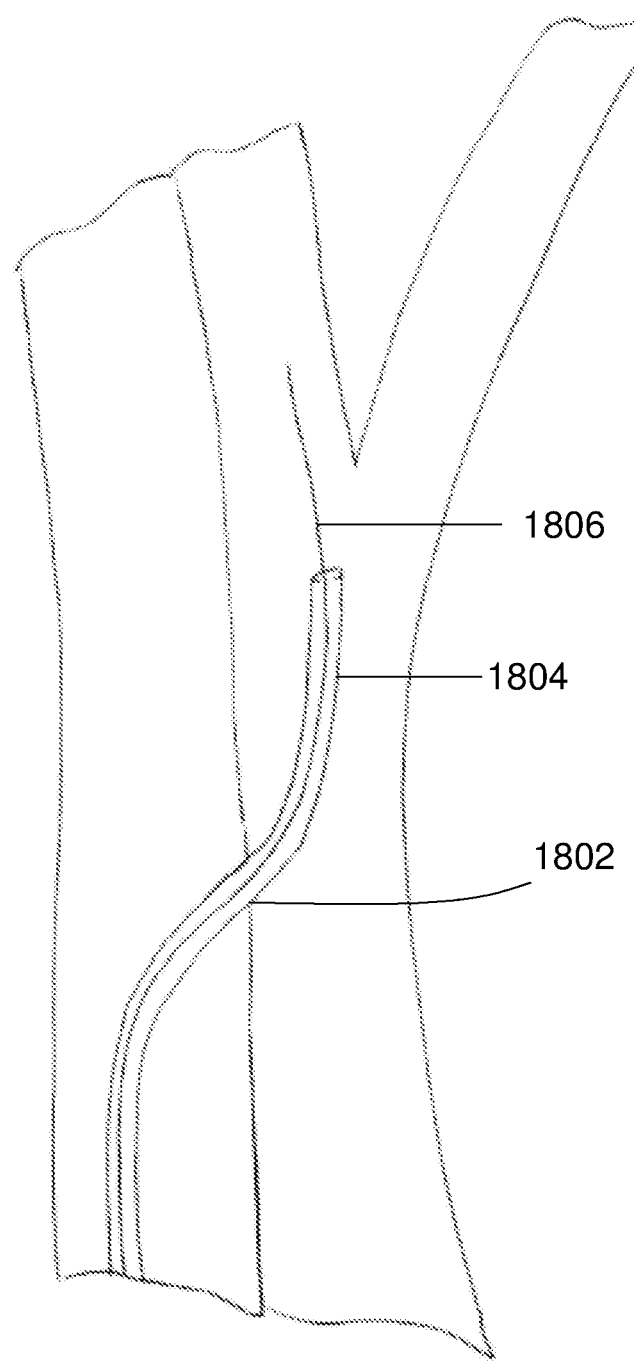
FIG. 18 illustrates a schematic cross-sectional view of the jugular vein and carotid artery following creation of trans-jugular carotid access.

As shown in FIG. 18, after gaining transjugular carotid access, an access sheath 1804 may be placed along a guide wire 1806 (e.g., guide wire 30, 0.035 wire) through the femoral vein 12 to the jugular vein 14 and into the carotid artery. The transjugular carotid fistula 1802 can then be dilated. In some embodiments, the dilation occurs sequentially, using dilators of increasing diameter (e.g., using Coons Taper Dilators from Cook Medical). In some embodiments, the dilators increase in size up to 10 F. The fistula can be dilated to about 3.2 mm, in some embodiments. Other diameters (e.g., about 2.5-3.9, 2.5, 2.7, 3.0, 3.2, 3.3, 3.5, mm, etc.) are also possible.

Figure 19A:
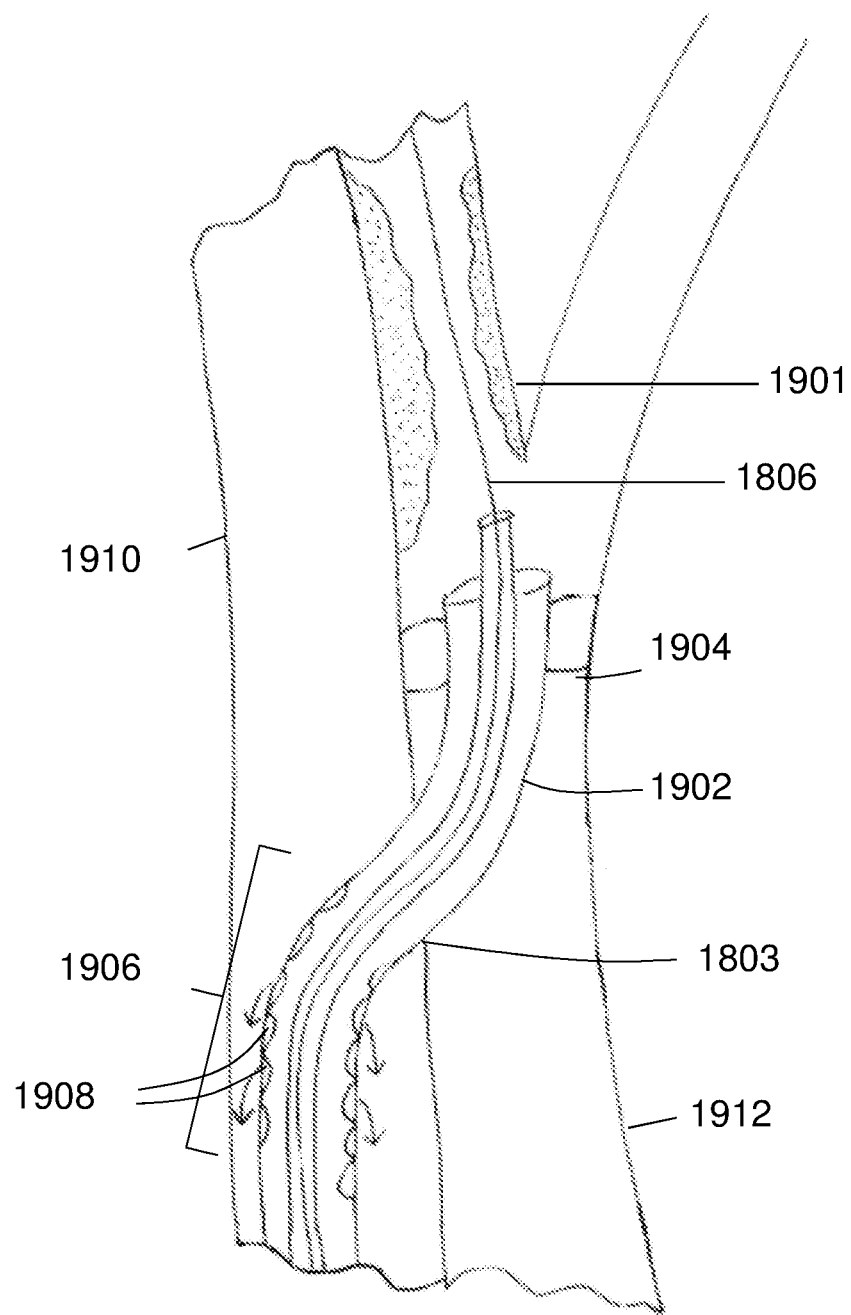
FIG. 19A illustrates a schematic view of an embodiment of a flow reversal sheath and working sheath advanced through a transjugular carotid fistula.
Figure 19B:
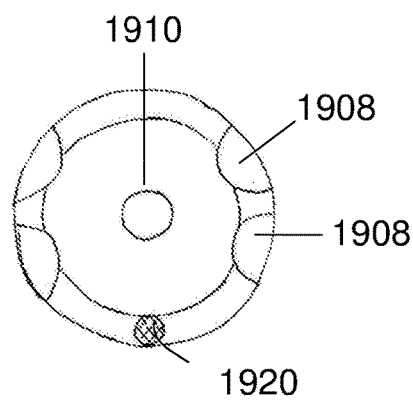
FIGS. 19B-D depict various views of an embodiment of a flow reversal sheath.
Figure 19C:
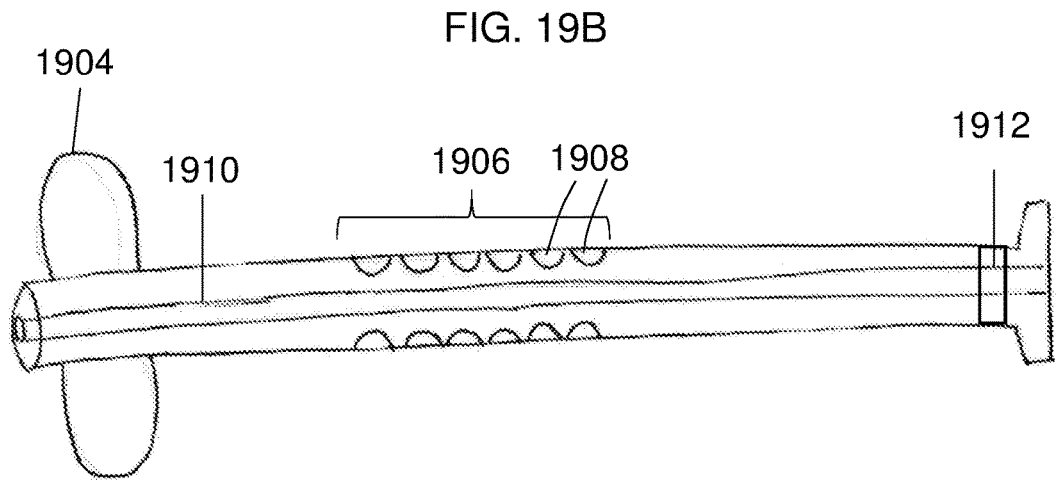
Figure 19D:
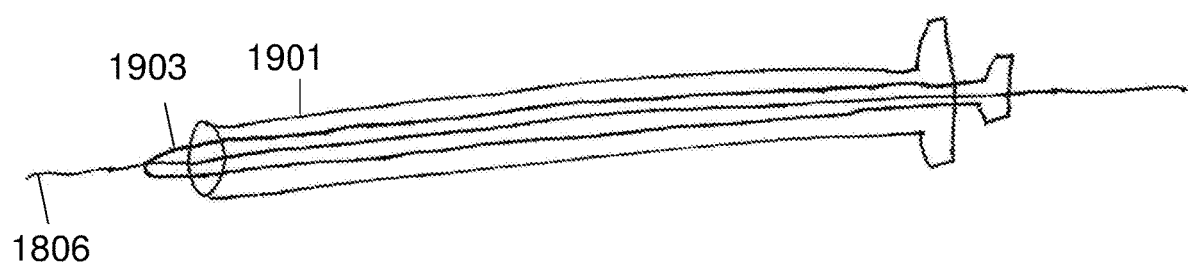

Moving to FIG. 19A, a trans jugular flow reversal sheath 1902, inner obturator 1903, and outer obturator 1901 (shown in side view of FIG. 19D) can be advanced through the vasculature over guidewire 1806, through the fistula 1803, and placed below the carotid bifurcation 1901. As shown in the side view of FIG. 19D, the inner obturator is positioned within inner channel 1910, described in more detail below. The outer obturator 1901 comprises a hollow sheath configured to be inserted within sheath 1902. The sheath 1902 can be sized to fit the diameter of the fistula or vice versa. For example, a 10 F sheath 1902 is used in some embodiments. FIG. 19C depicts a detailed view of the flow reversal sheath 1902. The flow reversal sheath 1902 comprises an occlusion balloon 1904 positioned near a distal end of the sheath 1902. In some embodiments, the balloon 1904 is positioned about 1 cm from a distal end of the sheath 1902.

Other distances are also possible (e.g., about 0.5-2 cm, about 0.5 cm, about 0.75 cm, about 1.25 cm, about 1.5 cm, about 2 cm, greater than 2 cm, etc.) The balloon 1904 is configured to occlude carotid inflow around the sheath 1902 to direct blood flow into the sheath 1902. The balloon 1904 can have a diameter of about 10-12 mm. The size of the balloon can be chosen to ensure a good seal between sidewalls of the carotid artery and the balloon. The balloon can be inflated under fluoroscopy to ensure proper occlusion of carotid inflow.

A flow reversal portion 1906 of the sheath 1902 comprises a plurality of holes 1908 positioned in sidewalls of the sheath 1902. The flow reversal portion 1906 can be positioned about 5 cm from the distal end of the sheath 1902. Other distances are also possible (e.g., about 4-6 cm, 3 cm, 4 cm, 6 cm, 7 cm, etc.). The distance from the distal end of the sheath can ensure the holes 1908 are properly positioned within the jugular vein while also allowing access to the carotid artery. The flow reversal portion 1906 can be about 10 cm long. Other lengths are also possible (e.g., about 8-12 cm, 7 cm, 8 cm, 9 cm, 11 cm, 12 cm, etc.). In some embodiments, the flow reversal portion comprises holes positioned circumferentially around the sheath 1902. As shown in the cross sectional view of FIG. 19B, a cross section of the sheath 1902 can comprise four holes positioned around a circumference of the sheath. Two pairs of holes can be positioned on diametrically opposing sides of the sheath 1902. In some embodiments, the holes comprise a different configuration (e.g., spaced equally around a circumference of the sheath, arranged on one side of the sheath, etc.). Other numbers of holes are also possible (e.g., 1, 2, 3, 5, 6, 7, 8, or more). In some embodiments, holes are positioned around only a portion of the circumference of the sheath 1902. Holes can be positioned at 1, 2, 3, 4, 5, 6, or more points around a portion or the entire circumference of the sheath. In some embodiments, there are about 6 or 7 holes positioned longitudinally along the sheath, not counting the holes positioned circumferentially. In other words, each of the seven holes positioned longitudinally may have additional holes positioned along a same radial plane of the sheath. Other amounts of holes positioned longitudinally along the sheath are also possible (e.g., about 5-10, 5, 8, 9, 10, or more holes). In some embodiments, the holes may comprise a spiral pattern extending longitudinally along the sheath. The holes can comprise a generally circular shape, as shown in the figures. Other shapes are also possible (e.g., elliptical, rectangular, square, triangular, etc.). In some embodiments, the flow reversal region can comprise slits or differently shaped and configured openings in the flow reversal region.

The flow reversal sheath 1902 comprises at least one inner channel 1910. The channel can be rigid and impervious and can be sized to accommodate a working sheath or catheter (e.g., a 6 F sheath). The sheath 1902 can comprise a length of about 90 cm. Other lengths (e.g., about 75-195 cm, 85-95 cm, 80 cm, 85 cm, 95 cm, 100 cm, greater than 100 cm, etc.) are also possible. A hemostatic valve 1912 is positioned at a proximal end of the sheath 1902. As shown in the cross sectional view of FIG. 19C, the sheath 1902 comprises a balloon inflation channel 1920 configured to communicate inflation fluid to the balloon 1904.

The flow reversal portion 1906 is positioned in the internal jugular vein 1910. The outer obturator 1901 can be removed to allow blood in the flow reversal sheath 1902 to flow through the flow reversal portion 1906. Allowing the blood within the sheath 1902 access to the jugular vein 1910 through the holes 1908 will cause the blood to move from a higher pressure area within the common carotid artery 1912 to the lower pressure area in the jugular vein 1910, reversing the flow of blood in the carotid arteries. The blood flows into the jugular vein through the flow reversal portion 1906 via holes 1908 as indicated by the arrows in FIG. 19A.

The guidewire 1806 and inner obturator 1903 can be withdrawn. A working sheath 1905 (e.g., a 90 cm long, 6 F sheath) can be advanced through the flow reversal sheath (FIG. 19A). The working sheath can be used to perform a carotid intervention (e.g., carotid stenting). Once the intervention is performed, the working sheath 1905 can be removed.

Balloon tamponade of the fistula can be performed to minimize bleeding occurring at the fistula. A guidewire can be advanced across the transjugular access point and into the common carotid artery. A balloon (e.g., a 12 mm angioplasty balloon) can be placed across the transjugular access point. The sheath 1902, guidewire, and balloon can be withdrawn into the jugular vein. The balloon is inflated on the jugular side of the access point for about 3-5 minutes. The balloon is removed. In some embodiments, balloon tamponade is performed for about 3-5 minutes. In some embodiments, the balloon tamponade is enough to sufficiently treat the opening between the jugular vein and the carotid artery to finish the procedure.

Figure 20:
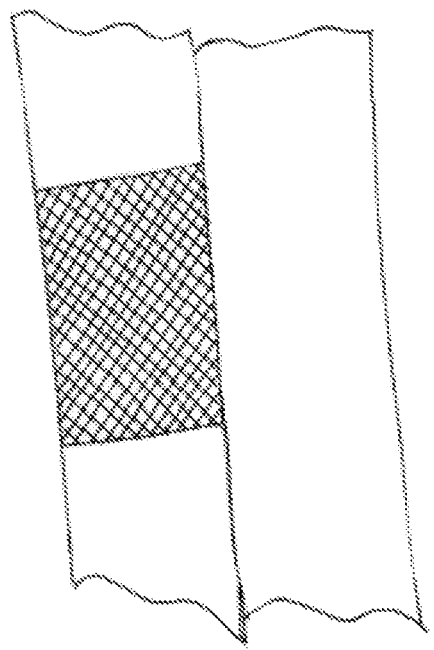
FIG. 20 illustrates a schematic view of a stent deployed in the jugular vein following a carotid intervention.

In some embodiments, a stent can then be placed across the access point in the jugular vein, shown in FIG. 20. The mesh can comprise a tightly woven absorbable material which can limit bleeding and induce thrombosis. In some embodiments, the mesh is configured to be absorbed in about 18 months. Other times are also possible (e.g., 6 months, 12 months, 2 years, etc.). The stent being absorbable can help minimize scar formation at the fistula site.

The sheath is removed from the jugular vein and from the patient. Manual pressure can be held over the puncture site.

Figure 21:
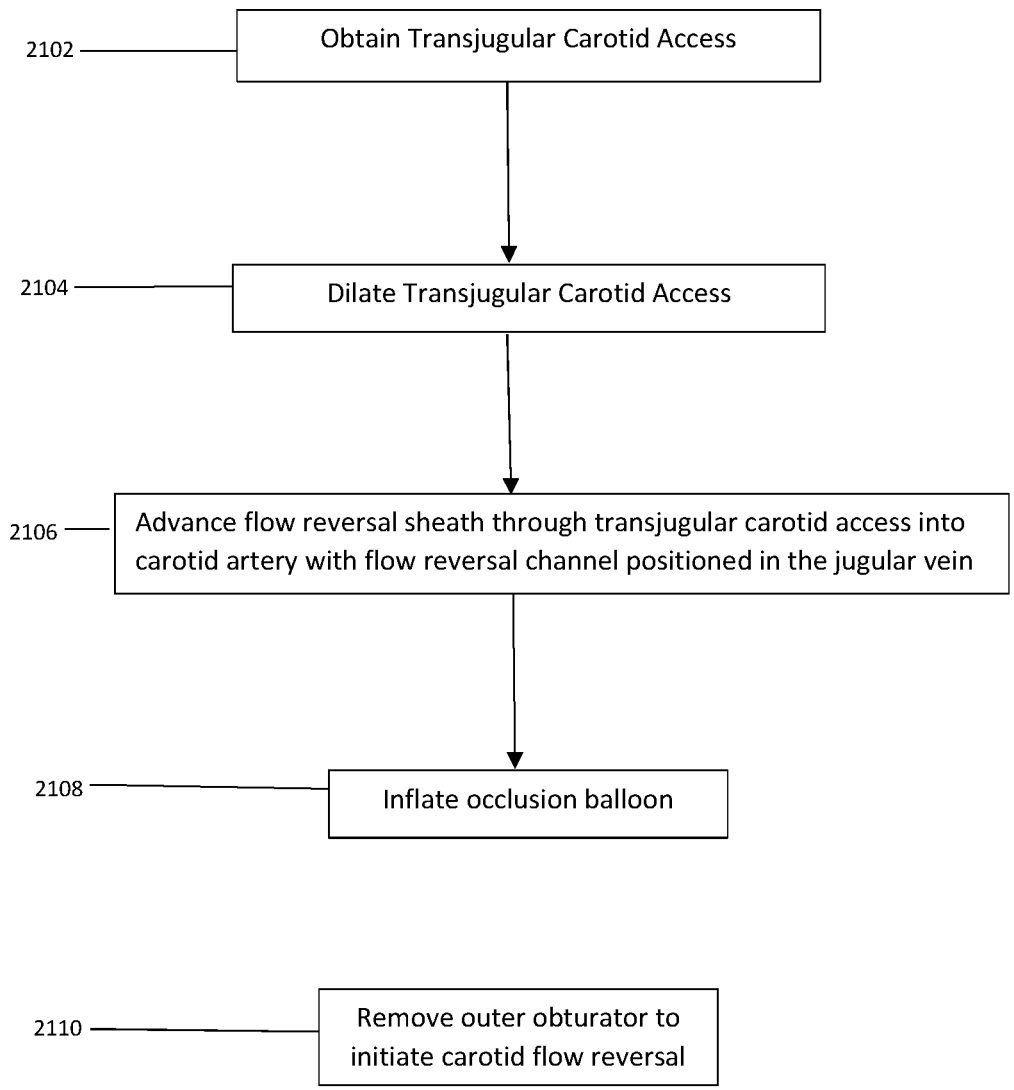
FIG. 21 illustrates a flowchart of an embodiment of a method of performing transjugular carotid flow reversal.

FIG. 21 depicts an embodiment of a method of performing transjugular carotid flow reversal, such as transjugular carotid flow reversal during carotid intervention. The method includes obtaining transjugular carotid access, shown at box 2102. As described above, obtaining transjugular carotid access can comprise obtaining femoral vein access percutaneously. A vascular sheath (e.g., 12 F, 10 cm sheath) can be used. A guidewire (e.g., a 0.035 mm guidewire) can be passed into the jugular vein. A transjugular access kit as described above with respect to FIGS. 1-12 can be used to perform transjugular carotid access and place a sheath (e.g., 6 F, 80 cm sheath) in the common carotid artery.

The method also comprises dilating the transjugular carotid access, as shown at box 2104. The transjugular carotid fistula can be sequentially dilated (e.g., using tapered tip vessel dilators). In some embodiments, the dilators increase in diameter up to 10 F. The dilators can have a length of about 80 cm.

The method comprises advancing a flow reversal sheath through the transjugular carotid access into the carotid artery, as shown at box 2106. The flow reversal sheath can be advanced to a location between the carotid bifurcation.

As shown at box 2108, the method includes inflating an occlusion balloon on the flow reversal sheath as described above with respect to FIGS. 19A-D. An outer obturator of the flow reversal sheath can be removed to initiate flow reversal, as shown at box 2110.

As described above, in some embodiments, the method further includes removing an inner obturator of the flow reversal sheath and passing a working sheath into the carotid artery to perform a carotid intervention. The working sheath can be removed following the intervention.

The method can comprise advancing a guidewire across the transjugular carotid access point and into the common carotid artery. An angioplasty balloon can be placed across the access point. The sheath, balloon, and guidewire can be retracted into the jugular vein. The balloon can be inflated on the jugular side of the access point for about 3-5 minutes. The balloon can be removed. A stent (e.g., comprising tightly woven, absorbable mesh) can be placed across the access point in the jugular vein.

The method can comprise removing the flow reversal sheath from the jugular vein and removing the original entry sheath from the vascular access point (e.g., the femoral vein). Manual pressure can be placed over the puncture site.

Any part or all of the above described methods can be done under fluoroscopic guidance.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for reversing flow in a carotid artery of a patient, comprising:
advancing a guidewire from a jugular vein and into the carotid artery through an opening between the jugular vein and the carotid artery;
advancing an obturator over the guidewire;
dilating the opening with the obturator;
advancing a flow reversal sheath over the guidewire through the dilated opening so that a distal end of the flow reversal sheath is positioned in the carotid artery; and
inflating a balloon positioned proximal to the distal end of the flow reversal sheath to reverse flow in the carotid artery and to cause blood to flow from the carotid artery through the flow reversal sheath and into the jugular vein, thereby reversing flow in the carotid artery.

2. The method of claim 1, further comprising advancing a working sheath through an inner lumen of the flow reversal sheath and into the carotid artery.

3. The method of claim 1, further comprising performing a carotid intervention after reversal of blood flow in the carotid artery.

4. The method of claim 1, further comprising performing balloon tamponade of the opening.

5. The method of claim 1, further comprising implanting a stent in the jugular vein across the opening.

6. The method of claim 1, wherein dilating the opening comprises dilating the opening to a diameter of about 3.2 mm.

7. The method of claim 1, wherein the flow reversal sheath comprises a distal opening in the distal end, the inflating step comprising inflating the balloon around a circumference of the flow reversal sheath to occlude blood flow around the flow reversal sheath.

8. The method of claim 1, wherein the flow reversal sheath comprises a distal opening in the distal end and a plurality of openings in a side wall proximal to the distal end, the method further comprising allowing blood to flow from the carotid artery into the distal opening the distal end and out of the plurality of openings in the side wall into the jugular vein.

9. The method of claim 1, further comprising forming the opening with a puncture needle prior to the step of advancing a guidewire.

10. The method of claim 9, wherein the step of advancing a guidewire comprises advancing the guidewire through the puncture needle.

11. A method for reversing flow in a carotid artery of a patient, comprising:
advancing a vascular catheter in a jugular vein of the patient;
advancing a stylet of the vascular catheter from the jugular vein, through a wall of the jugular vein and then through a wall of the carotid artery to form an opening between the jugular vein and the carotid artery;
advancing a flow reversal sheath through the opening so that a distal end of the flow reversal sheath is positioned in the carotid artery; and
inflating a balloon positioned proximal to the distal end of the flow reversal sheath to reverse flow in the carotid artery and to cause blood to flow from the carotid artery through the flow reversal sheath and into the jugular vein, thereby reversing flow in the carotid artery.

12. The method of claim 11, further comprising enlarging the opening with an obturator.

13. The method of claim 11, further comprising advancing a guidewire through the opening, the step of advancing a flow reversal sheath comprising advancing the flow reversal sheath over the guidewire.

14. The method of claim 11, further comprising performing a balloon tamponade of the opening.

15. The method of claim 11, further comprising advancing a working sheath through an inner lumen of the flow reversal sheath and into the carotid artery.

16. The method of claim 11, further comprising performing a carotid intervention after reversal of blood flow in the carotid artery.

17. The method of claim 11, further comprising implanting a stent in the jugular vein across the opening.

18. The method of claim 11, wherein the flow reversal sheath comprises a distal opening in the distal end, the inflating step comprising inflating the balloon around a circumference of the flow reversal sheath to occlude blood flow around the flow reversal sheath.

19. The method of claim 11, wherein the flow reversal sheath comprises a distal opening in the distal end and a plurality of openings in a side wall proximal to the distal end, the method further comprising allowing blood to flow from the carotid artery into the distal opening the distal end and out of the plurality of openings in the side wall into the jugular vein.

20. The method of claim 11, wherein the step of advancing a vascular catheter in a jugular vein of the patient comprises inserting the vascular catheter into a femoral vein and advancing the vascular catheter from the femoral vein into the jugular vein.

21. The method of claim 11, wherein the step of advancing a vascular catheter in a jugular vein of the patient comprises inserting the vascular catheter into a vein in the patient's arm and advancing the vascular catheter from the vein in the patient's arm into the jugular vein.

* * * * *